(12) United States Patent
Damadian et al.

(10) Patent No.: US 6,504,371 B1
(45) Date of Patent: Jan. 7, 2003

(54) MRI MAGNET WITH ENHANCED PATIENT ENTRY AND POSITIONING

(75) Inventors: Timothy Damadian, Syosset, NY (US); Gordon Danby, Wading River, NY (US); Raymond V. Damadian, Woodbury, NY (US); Hank Hsieh, Berkeley, CA (US); James J. Persoons, East Northport, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 10/136,939

(22) Filed: May 1, 2002

Related U.S. Application Data (63) Continuation of application No. 09/789,460, filed on Feb. 21, 2001, now Pat. No. 6,414,490, which is a continuation of application No. 08/978,084, filed on Nov. 25, 1997, now abandoned, which is a continuation-in-part of application No. 08/975,913, filed on Nov. 21, 1997, now Pat. No. 6,201,394, which is a continuation-in-part of application No. 07/993,072, filed on Dec. 18, 1992, now Pat. No. 6,023,165.
(60) Provisional application No. 60/031,610, filed on Nov. 27, 1996, and provisional application No. 60/032,589, filed on Nov. 29, 1996.

(51) Int. Cl.[7] .................................................. G01V 3/00
(52) U.S. Cl. ........................ 324/318; 324/319; 600/415
(58) Field of Search ................................. 324/318, 319, 324/320, 300, 306, 307, 309; 600/415, 421, 427, 410

(56) References Cited

U.S. PATENT DOCUMENTS

| 4,534,076 A | 8/1985 | Barge |
|---|---|---|
| 4,534,358 A | 8/1985 | Young |
| 4,629,989 A | 12/1986 | Riehl et al. |
| 4,829,252 A | 5/1989 | Kaufman |
| 4,908,844 A | 3/1990 | Hasegawa |
| 4,924,198 A | 5/1990 | Laskaris |
| 4,968,937 A | 11/1990 | Ali Akgun |
| 4,985,678 A | 1/1991 | Gangarosa et al. |
| 5,008,624 A | 4/1991 | Yoshida |
| 5,065,761 A | 11/1991 | Pell |
| 5,153,546 A | 10/1992 | Laskaris |
| 5,155,758 A | 10/1992 | Vogl |
| 5,162,768 A | 11/1992 | McDougall et al. |
| 5,197,474 A | 3/1993 | Englund et al. |
| 5,305,365 A | 4/1994 | Coe |
| 5,305,749 A | 4/1994 | Li et al. |

(List continued on next page.)

FOREIGN PATENT DOCUMENTS

JP        1-242056        9/1989

* cited by examiner

Primary Examiner—Louis Arana
(74) Attorney, Agent, or Firm—Lerner, David, Littenberg, Krumholz & Mentlik, LLP

(57) ABSTRACT

A magnetic resonance imaging (MRI) magnet in combination with a mobile patient-positioning device, including a patient support and a method of using same for positioning patients for MRI scanning. The patient support is rotatable through a range of orientations from a horizontal to a vertical position, including being lockable at any oblique angle with respect to the horizontal. The patient disposed on the patient-positioning device in a predetermined orientation can then be moved horizontally into and out of a patient-receiving space in the MRI magnet at the predetermined angle or orientation. A preferred embodiment includes a plurality of patient-positioning devices in which a series of patients can be placed in a ready state while one patient is within the patient-receiving space. As an alternative embodiment, the patient may be moved vertically into position for MRI scanning by way of an elevator which is actuatable from the floor below the patient receiving space. This elevator also may be used in combination with the patient-positioning device. Preferred embodiments facilitate MRI guided surgery and other procedures performed while the patient is being imaged.

7 Claims, 9 Drawing Sheets

U.S. PATENT DOCUMENTS

| | | |
|---|---|---|
| 5,349,956 A | 9/1994 | Bonutti |
| 5,386,447 A | 1/1995 | Siczek |
| 5,436,607 A | 7/1995 | Chari et al. |
| 5,475,885 A | 12/1995 | Ishikawa |
| 5,592,090 A | 1/1997 | Pissanetzky |
| 5,606,970 A | 3/1997 | Damadian |
| 5,623,241 A | 4/1997 | Minkoff |
| 5,640,958 A | 6/1997 | Bonutti |
| 5,735,278 A | 4/1998 | Hoult et al. |
| 5,743,264 A | 4/1998 | Bonutti |
| 5,779,637 A * | 7/1998 | Palkovich et al. .......... 324/318 |
| 5,983,424 A | 11/1999 | Naslund |
| 6,246,239 B1 | 6/2001 | Krogmann et al. |
| 6,411,088 B1 * | 6/2002 | Kuth et al. ................. 324/307 |
| 6,414,490 B1 * | 7/2002 | Damadian et al. .......... 324/319 |

MRI MAGNET WITH ENHANCED PATIENT ENTRY AND POSITIONING

CROSS REFERENCE TO RELATED APPLICATIONS

The present application claims the benefit of U.S. Provisional Application Nos. 60/031,610, filed Nov. 27, 1996 and 60/032,589, filed Nov. 29, 1996, the disclosures of which are hereby incorporated by reference herein. The present application is a continuation of and also incorporates herein by reference the disclosure of U.S. patent application Ser. No. 09/789,460 filed Feb. 21, 2001 now U.S. Pat. No. 6,414,490, which application is a continuation of and also incorporates herein by reference the disclosure of co-pending, commonly assigned U.S. patent application Ser. No. 08/978,084 filed Nov. 25, 1997 now abandoned, which is a continuation-in-part of U.S. patent application Ser. No. 07/993,072, filed Dec. 18, 1992 now U.S. Pat. No. 6,023,165, and U.S. patent application Ser. No. 08/975,913, filed Nov. 21, 1997 now U.S. Pat. No. 6,201,394.

BACKGROUND OF THE INVENTION

The present invention relates generally to magnetic resonance imaging or "MRI" and particularly to an apparatus and methods for entering and positioning a patient into an MRI system.

The magnetic resonance or "MR" scanners commonly used today require a patient who is to be scanned to be oriented with the long axis of the body in a horizontal position. This aspect of MR scanners or MRI is the result, in part, of the magnet design, the patient-positioning system used to position the patient within the magnet, and the methods designed to accommodate these features of the MRI device.

Thus, of necessity, MRI normally is restricted to the situation where gravitational force is exerted on the human body when it is horizontally oriented. However, a human body has other natural positions. These are upright or vertical positions, or sitting positions, where the forces on the body are effectively rotated 90 degrees with respect to the horizontal orientation. MR scanning of the body, oriented in a vertical or sitting position, is not presently achievable with commercially available systems.

Attempts have been made heretofore to provide MR scanning of a patient in a vertical position. For example, in U.S. Pat. No. 5,153,546, a superconductive air-core MRI magnet is shown which can be rotated by an operator so that a patient can walk into a patient receiving space within the magnet and be imaged. However, when in the patient receiving space of this reference, the patient does not have any support for sustaining and maintaining the patient's relative orientation and position. Also, once the magnet has been rotated to accommodate a patient in a vertical orientation, there would be no room for a physician or attending personnel to access the patient during a scan. Also, if it is desirable to have a second patient scanned in a horizontal orientation, the MRI magnet would have to be rotated back to the original position by the operator. This would cause a delay before the next patient can be scanned.

Thus, it is desirable to have an apparatus and methods which would permit MR scanning to be performed with the human body oriented in a vertical or near vertical position or in a sitting position where the MRI magnet does not necessarily have to change its orientation. It also is desirable to have a patient support or rest to accommodate various orientations of the patient. Further, it is desirable to have an apparatus and methods which provide for a series of patients to be scanned in a time saving manner.

SUMMARY OF THE INVENTION

The present invention addresses these needs. The preferred apparatus and methods of this invention allow such vertical or near vertical orientation during scanning, and, most preferably, also allow other orientations of the patient. The present invention also may provide enhanced efficiency and convenience in scanning multiple patients. In addition to providing a vertical or near vertical orientation during scanning, a preferred embodiment allows a physician and associated medical personnel to have access to the patient during a scanning session so as to, by way of example, perform MRI-assisted surgery.

One aspect of the present invention provides a method of magnetic resonance imaging comprising the steps of: positioning a first patient to be scanned in a patient-receiving space of a magnetic resonance imaging magnet and conducting a magnetic resonance scan of the first patient; during the magnetic resonance scan of the first patient, positioning a second patient in a desired orientation on a mobile patient-positioning device disposed remote from the patient-receiving space; moving the first patient out of the patient-receiving space and moving the second patient into the patient-receiving space by moving the mobile patient-positioning device while maintaining the second patient in the desired orientation; and conducting a magnetic resonance scan of the second patient while the second patient is disposed in the patient-receiving space on the mobile patient-positioning device.

A further aspect of the present invention provides a method of magnetic resonance imaging comprising the steps of: positioning a series of patients on a plurality of mobile patient-positioning devices so that each patient is disposed on one associated mobile patient-positioning device which is brought to a desired orientation for that patient while the patient and the associated mobile patient-positioning device are disposed remote from a patient-receiving space of a magnetic resonance imaging magnet; moving the patients into and out of the patient-receiving space in sequence by moving the mobile patient-positioning devices so that each patient is moved into the patient-receiving space while such patient is maintained iii the desired orientation; and conducting magnetic resonance scans of the patients, the aforesaid steps being coordinated so that at least some of the patients are brought to the desired orientation while other patients are disposed in the patient-receiving space.

Yet another aspect of the present invention provides a mobile patient-positioning device comprising: a frame; a patient support mounted to the frame for movement through a range of orientations relative to the frame; means for allowing movement of the frame relative to a magnetic resonance imaging magnet so that a patient on the patient support can be positioned in a patient-receiving space of such magnet with the support in any orientation. Preferably, the means for allowing movement includes wheels supporting the frame. The foregoing arrangements facilitate rapid scanning of patients in sequence. The MRI system need not remain idle while a new patient is adjusted to the proper position.

Desirably, the mobile patient-positioning device further comprises means for lifting the patient support upwardly and downwardly relative to the frame.

Alternatively or additionally, an embodiment of the present invention includes a mobile patient-positioning device in combination with an elevator mounted in a fixed location relative to the magnet, the elevator being adapted to move the frame upwardly and downwardly relative to the magnet when the frame is disposed adjacent the magnet. The arrangements allow scanning of various parts of the patient's body.

A further aspect of the present invention provides a magnetic resonance imaging magnet comprising: a magnet frame; a pair of pole faces spaced apart from one another along a horizontal pole axis and defining a patient-receiving space therebetween; supports holding the frame on or above a floor of a structure so that a patient may enter the patient-receiving space by moving across the floor of the structure; and magnetic flux generating means for providing magnetic flux in the patient-receiving space.

Preferably the magnet may further comprise an elevator for raising or lowering a patient relative to the frame. More preferably, the elevator has a platform and the elevator is arranged to move the platform into a boarding position wherein the platform is close to the floor so that a patient standing on the floor of the structure can step onto the platform or can be wheeled onto the platform on a wheeled carriage.

In another preferred embodiment of the present invention, there is provided an MRI magnet comprising a magnet frame; a pair of pole faces spaced apart from one another along a horizontal pole axis and defining a patient-receiving space therebetween; supports for holding the frame on or above the floor of a structure so that a patient may enter the patient-receiving space by moving across the floor of the structure; and magnetic flux generating means for providing magnetic flux in the patient-receiving space; in combination with a mobile patient-positioning device. The mobile patient-positioning device includes a frame; a patient support mounted to the frame for movement through a range of orientations relative to the frame; and means for allowing movement of the frame relative to the magnet so that a patient on the patient support can be positioned in a patient-receiving space of the magnet with the patient support in any desired orientation.

Preferably, the frame is a ferromagnetic frame providing a flux return path between the poles. Desirably, the frame is generally C-shaped.

More preferably, the flux generating means is arranged to provide a magnetic field strength of at least about 3 kilogauss in the patient-receiving space.

DETAILED DESCRIPTION OF THE PREFERRED EMBODIMENTS

Apparatus in accordance with one embodiment of the present invention, as shown in FIGS. 1–8, includes a magnetic resonance imaging magnet 9 which may include a ferromagnetic flux return frame or yoke 10 defining a pair of opposed poles 12 projecting towards one another along a horizontally-oriented pole axis 14 (FIG. 2) and defining a patient receiving space 16. Flux generating means such as permanent magnets associated with frame 10, superconducting coils encircling portions of the flux return frame 10 or, most preferably, resistive electrical coils 18 encircling portions of the frame 10 are provided. As illustrated, the resistive coils 18 encircle the frame 10 adjacent poles 12. The structure of the C-shaped magnet may be as illustrated and described in co-pending, commonly assigned U.S. patent application Ser. No. 07/993,072 filed Dec. 18, 1992, the disclosure of which is hereby incorporated by reference herein. The magnet defines an open direction of patient entry as indicated by arrow 20 in FIG. 1, allowing movement of a patient into patient receiving space 16. The magnet is supported on a floor 22 of a building, vehicle or other structure by a set of columns 24, so that the pole axis 14 and the patient-receiving space 16 are disposed above the floor 22.

One or, more preferably, several mobile patient-positioning devices 30 are provided. One such device is shown in FIGS. 3–8. Each patient-positioning device is movable relative to the magnet 9 independently of the other patient-positioning devices. Thus, the preferred patient-positioning device 30 illustrated includes a frame 32 mounted on wheels 34 so that the device 30, with a patient thereon can be moved into and out of the patient-receiving space 16 of the magnet 9 by an operator manipulating the device 30 with a handle 36. The device 30 further includes a patient support 38 movably mounted to frame 32 as by a swingable pivot and lock arrangement 40 and linear movement device 42. Patient support 38 can be swung or adjusted between the horizontal position depicted in FIG. 3 and a vertical position depicted in FIG. 4, and also can be moved to tilted positions (see FIG. 6) at which the patient support 38 makes oblique angles with the horizontal. As an example of such an oblique angle, a patient may be placed in a Trendelenburg position and or a counter-Trendelenburg position. Generally, a Trendelenburg position is one where the patient support 38 is tilted from horizontal such that the patient's head is below his or her feet in relation to the horizontal. This position is useful during cardiac surgery and scanning in the heart region. A counter-Trendelenburg position is one where the patient's head is above their feet. Linear movement device 42 is arranged to move the patient support relative to pivot and lock arrangement 40 and frame 32. When the patient support 38 is in the vertical position (FIG. 4), the linear movement device 42 can move the patient support 38 upwardly and downwardly. Also, when the patient support 38 is in a vertical position, the support can be rotated about a vertical axis. When the patient support is in the oblique position, linear movement device 42 can move the patient support in the oblique plane. For example, linear movement device 42 may include a fluid-operable piston and cylinder arrangement. In place of wheels 34, frame 32 can be equipped with slidable skids or air cushion supports for raising the frame slightly off the floor to permit movement. The frame 32 of the mobile patient-positioning device 30 also may be supported for movement towards and away from the magnet on an overhead monorail or other elevated rail arrangement. Finally, device 30 may be automatically moved into and out of the patient receiving space by means of an automatic control device (not shown).

The patient support 38 is further equipped with a retractable or swingable foot stand 44; a retractable seat 46 and retractable hand grips or arm rests 48. A patient may be positioned on patient support 38 and brought to essentially any desired orientation relative to frame 32 and relative to the floor 22 or a horizontal position. For example, a patient may be positioned on support 38 in a standing position, with support 38 in a vertical or near vertical orientation and with the patient standing on foot rest 44. Preferably, the patient leans on support 38 while standing. The patient also may be positioned on seat 46. Alternatively, the patient may lie on the surface of patient support 38.

The components of the mobile patient-positioning device 30 are formed from non-metallic materials such as, for example and, preferably, polymers or other dielectric materials. Device 30 does not substantially interact with the magnetic fields produced by magnet 10 and thus does not impair the magnetic resonance imaging process.

A patient may be positioned on one mobile patient-positioning device 30 and brought to the desired position and orientation while that device 30 is remote from the magnet 9 and while the magnet 9 is being used to image another patient, preferably held on another, similar mobile patient-positioning device. Thus, the time consumed in positioning and orienting the patient does not detract from the productivity of the scanner, including magnet 9. The magnet 9 is only occupied by a given patient during the time required to conduct the actual scan of the patient and during very brief intervals required to wheel the mobile patient-positioning device 30, with the patient prepositioned thereon, into the patient receiving space 16. To assure accurate positioning of the mobile patient-positioning device relative to the magnet 9 and hence assure accurate positioning of the patient, the floor 22 or the magnet frame 10 itself may be equipped with rails or guides or tracks which mate with corresponding features on the mobile patient-positioning device 30. For example, wheels 34 may be grooved or flanged, and may run on rails or grooves in floor 22. A first set of rails, guides or tracks may run substantially in the direction of the patient entry 20. A second set of rails and the like may run substantially perpendicular to the first set. A second patient may be disposed on a patient-positioning device which is itself positioned to run on the second set of rails. In this manner, the second patient is positioned in a ready state, waiting to be moved into position for MRI scanning. Preferably, the first and second set of rails are positioned adjacent each other on the floor so that they intersect and allow for movement from one set to the other.

The ability to position each patient in essentially any orientation allows scanning while the patient is in essentially any posture. This improves the realism of the scanned image and allows detection of posture-dependent problems. For example, a patient having difficulties with a knee joint can be imaged while the joint is bearing weight, with the patient in an essentially standing position. Also, internal organs can be brought to the positions which they occupy while the patient is standing or seated. For example, it is advantageous to perform intestinal surgery on a patient when that person is in a vertical position. The ability to move the patient-positioning device upwardly and downwardly allows scanning of essentially any part of the patient. Typically, the pole axis 14 (FIG. 2) is about 5–6 feet (about 1.5–2.0 meters) above floor 22 so that the head of a standing adult patient can be positioned at or near the pole axis. The ability of the mobile patient-positioning device 30 to elevate the patient, by action of linear movement device 42 allows other parts of the patient to be brought into alignment with the plural axis and hence to be imaged. The magnetic flux return frame or yoke 10 and the coils may be hidden from the patient by a false or cosmetic wall surrounding the same.

Figure 9:
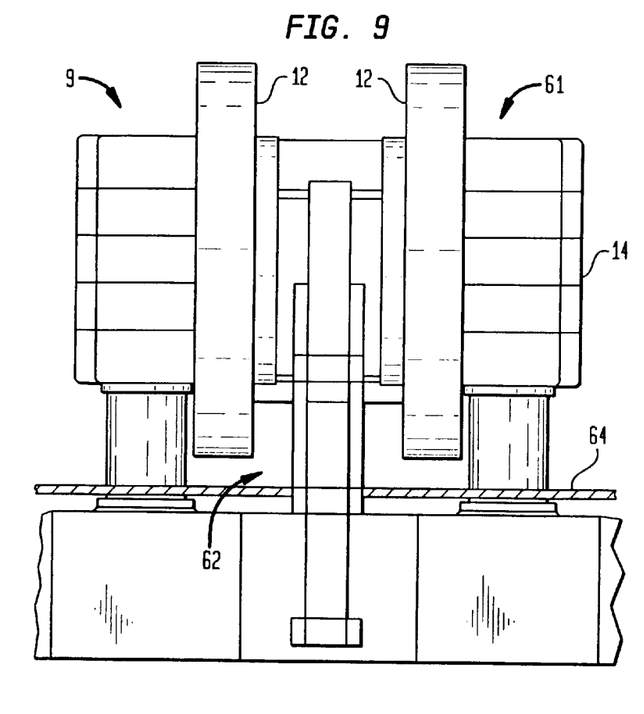
FIG. 9 is a front elevation view of the magnet of FIG. 1 and a patient-positioning device in accordance with a further embodiment of the invention.
Figure 10:
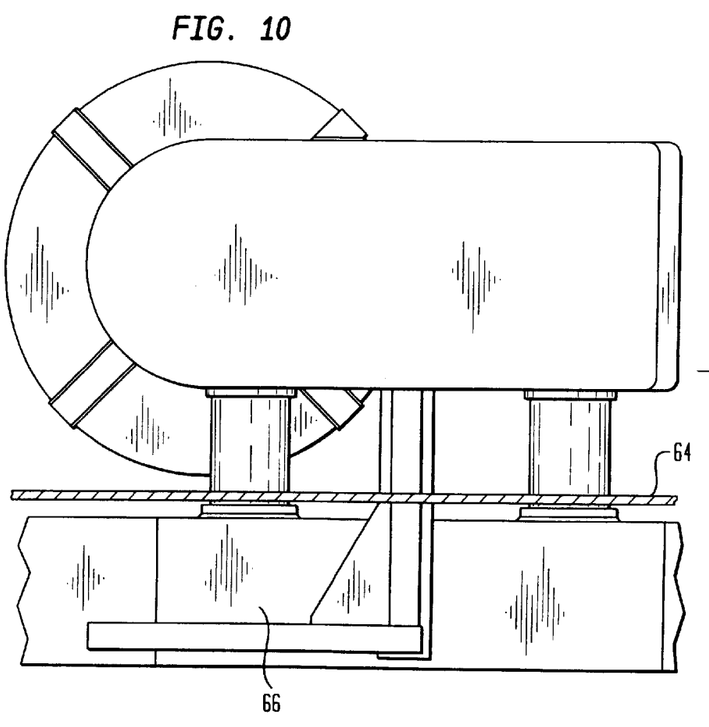
FIG. 10 is a side elevation view of the magnet and patient-positioning device of FIG. 9.
Figure 11:
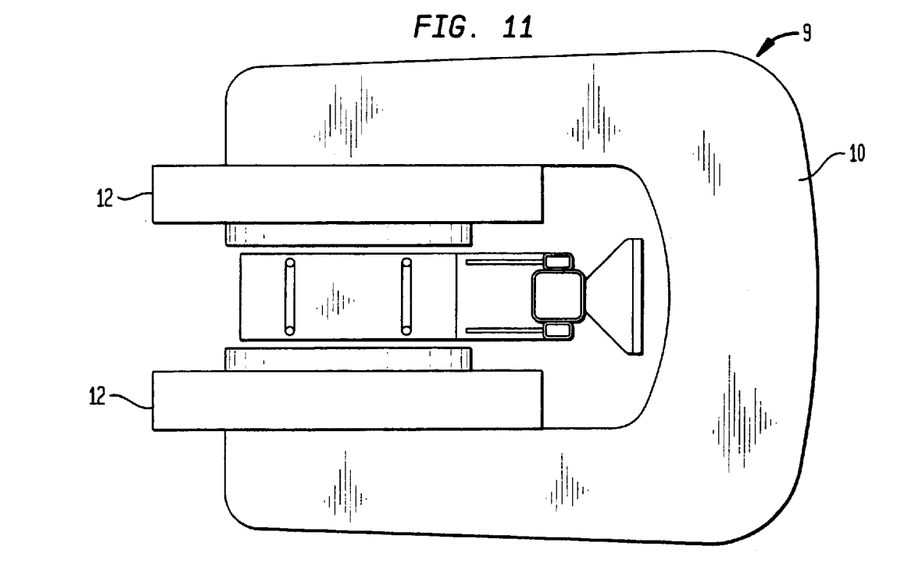
FIG. 11 is a plan view of the magnet and patient-positioning device of FIG. 9.

As illustrated in FIGS. 9, 10 and 11, a similar C-shaped magnet 61 may include a built-in patient elevator 62. The C-shaped magnet 61 may be positioned above a false floor 64 so that the patient may walk onto the elevator platform 66 while the platform 66 is aligned with the false floor 64 and the elevator platform 66 may then be raised or lowered to position the patient at the appropriate height relative to the magnet 61 and relative to the plural axis 14.

The two approaches described heretofore may be combined. Thus, a mobile patient-positioning device 30 as illustrated in FIGS. 1–8 may be used with a fixed patient elevator 60, so that the patient is positioned at the appropriate orientation on the mobile patient-positioning device. The device 30 is rolled onto the elevator platform 66. The elevator platform 66 is then raised and lowered as necessary.

In a further alternative, a fixed elevator need not incorporate a platform, but instead may be arranged to engage the frame 32 of the mobile patient-positioning device 30, as by a fork or rods on the elevator 62 engaging in holes on the frame of the mobile patient-positioning device 30.

Figure 4:
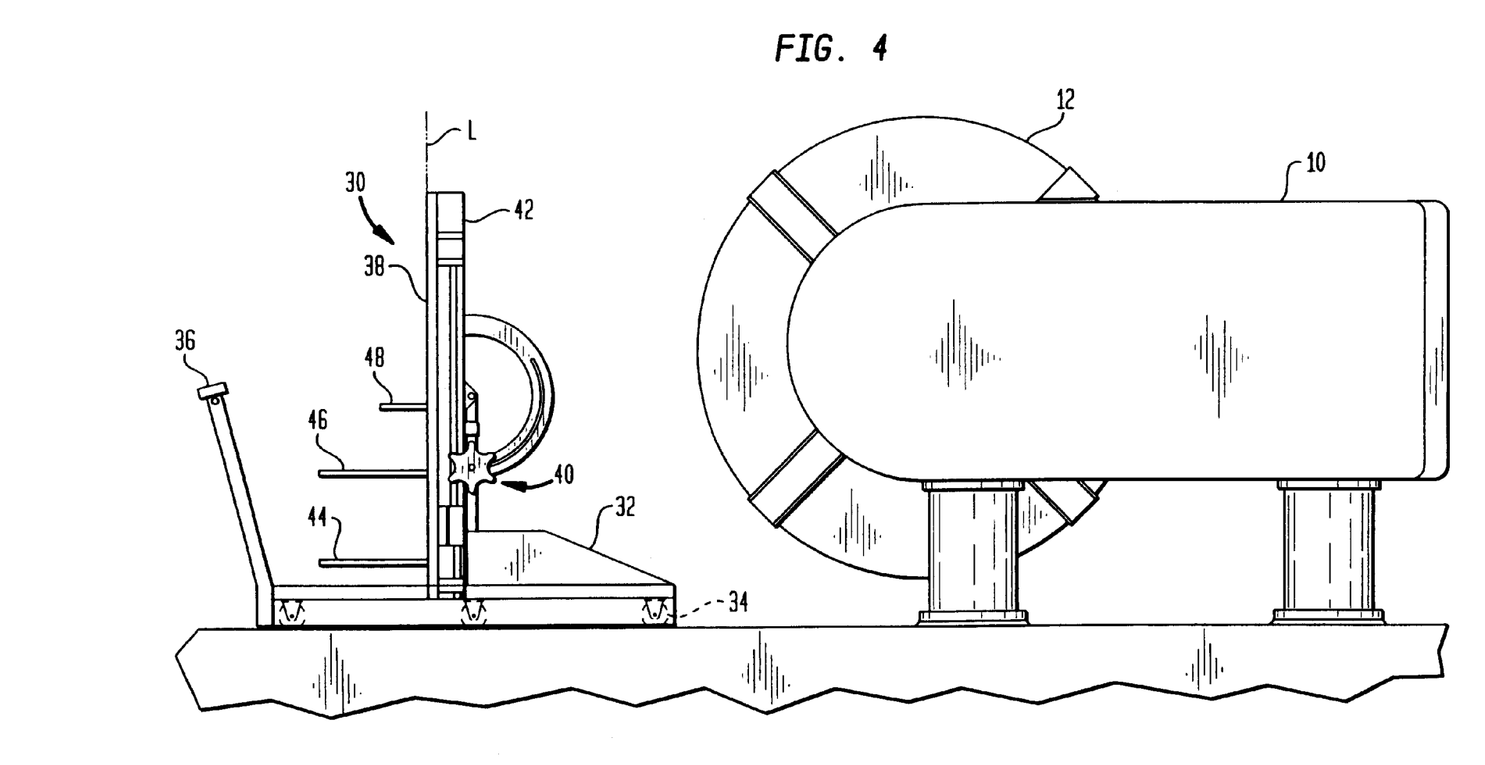
FIG. 4 is a side elevation view of the system of FIG. 3 showing the patient support of the patient-positioning device of FIG. 3 in a vertical position.
Figure 5:
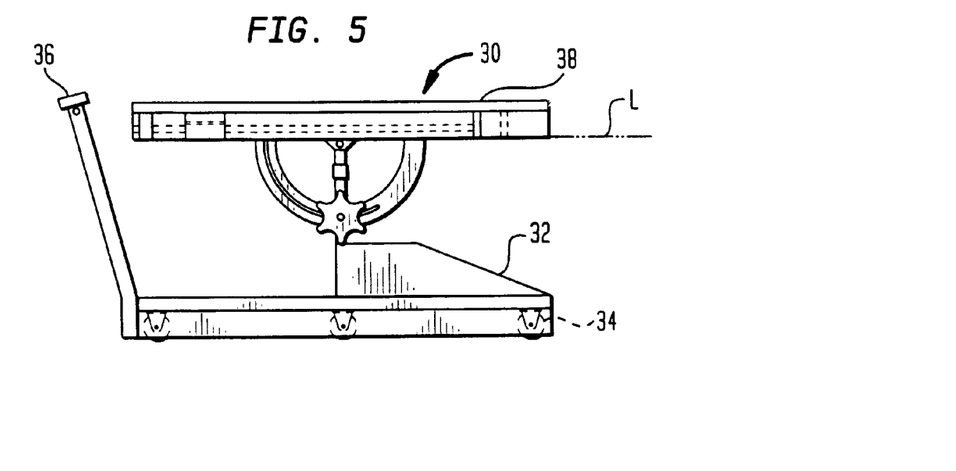
FIG. 5 is a side elevation view of the patient-positioning device of FIG. 3 showing the patient support of the patient-positioning device in a horizontal position.

A preferred method of MR Scanning of a patient with the long axis of the body in a vertical orientation would proceed as follows:

With the patient support 38 in a vertical position as shown in FIG. 4, the patient steps onto the retractable foot stand 44. During this stage of the method, the patient support 38 is maintained at a convenient height for the patient to step onto the foot stand 44 from the floor 22. Although foot stand 44 is depicted as slightly above the level of the floor in FIG. 4, the patient support 38 optionally may be lowered to position the foot stand level with the floor, thereby further facilitating access by infirm patients.

The patient is then positioned and made comfortable. This step may include the patient grasping the retractable hand grasps or arm rests 48. The patient also may lean on support 38 while standing. In addition, additional cushioning, such as pillows and inflatable supports, may be provided to increase the patient's comfort. The patient-positioning device 30 is then moved into the patient receiving space 16 where the additional positioning of the patient up or down is achieved by means of the linear movement device 38. This aspect of patient-positioning will locate the anatomical region of interest for MR scanning at the proper position in the patient receiving space 16. At this point, the MR scanning data acquisition will proceed.

Following completion of MRI data acquisition, the patient-positioning device 30 is removed from the patient receiving space 16. In this relocation step, the patient support 30 may be lowered or raised to a convenient height for the patient to step off of the foot stand 44 onto the floor 22. This may be accomplished before or after removing the patient-positioning device 30 from the patient receiving space 16. The patient may then dismount the patient-positioning device 30.

Figure 6:
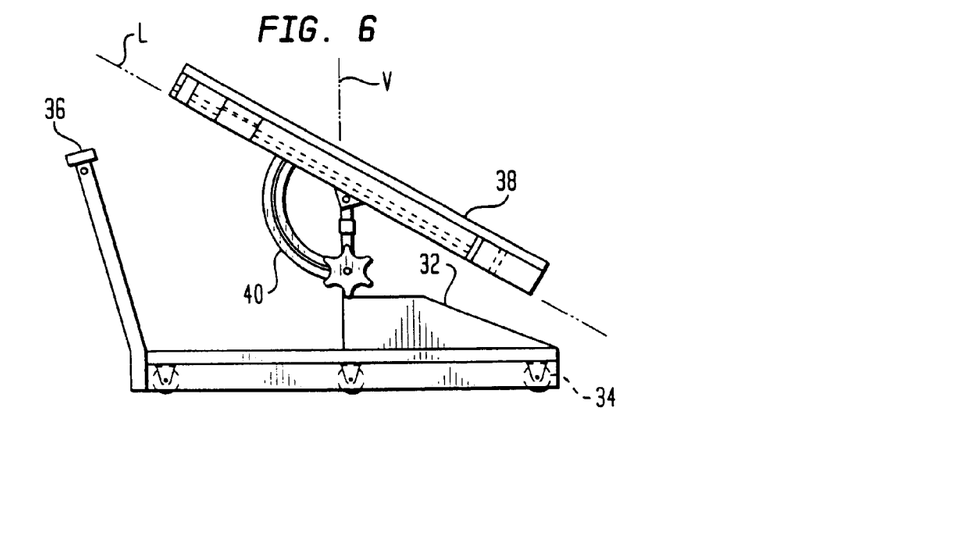
FIG. 6 is a side elevation view of the patient-positioning device of FIG. 3 showing the patient support of the patient-positioning device at a position between horizontal and vertical.
Figure 7:
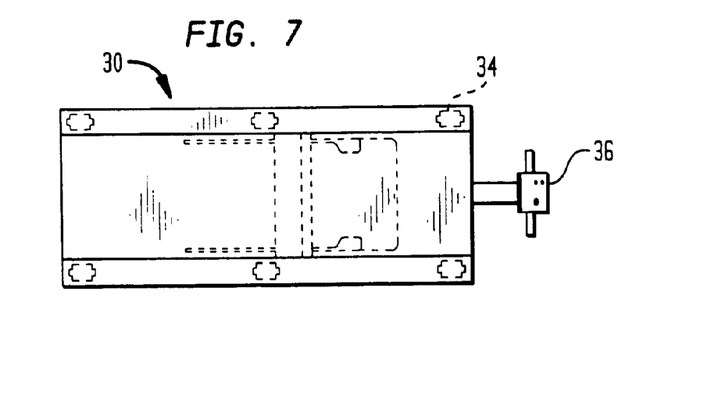
FIG. 7 is a top plan view of the patient-positioning device of FIG. 3.
Figure 8A:
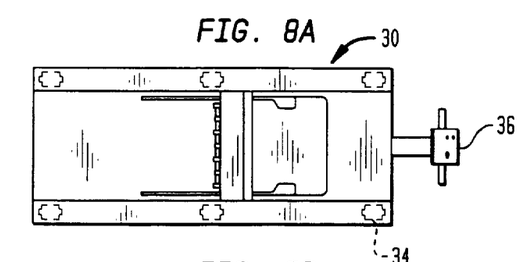
FIG. 8A is a top plan view of the patient-positioning device of FIG. 3 with the patient rest in the vertical position.
Figure 8B:
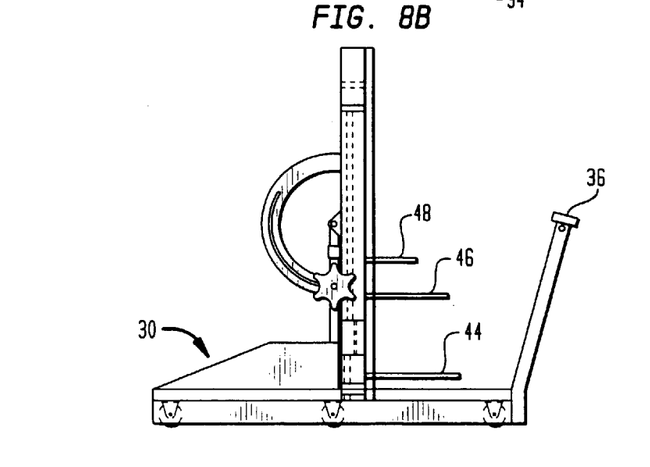
FIG. 8B is a side elevation view of the patient-positioning device of FIG. 8A.

There are variations of this preferred embodiment which should be evident in light of the foregoing description. First, the patient, when standing on the retractable foot stand, may be oriented in any direction as may be defined by rotation along the long axis of the patient's body. To this end, the pivot and lock arrangement 40 may be provided with additional pivots, gimbals or other mechanisms which allow patient support 38 to pivot relative to frame 32 about its long axis L or another axis parallel thereto, and/or to pivot about a vertical axis V relative to the frame (FIG. 6). Alternatively or additionally, the wheels 34 or other mobile support device supporting the frame 32 may include pivotable casters or other devices which allow the frame to be turned around a vertical axis relative to the floor 22. Also, slight deviations or tilts of the patient's body, and of the long axis L from the true vertical orientation may be used. Finally, if the objective of the MRI procedure is to scan an anatomical region of interest in the upper portion of the patient's body in a vertical orientation, the patient may be seated on retractable seat 46. In the preferred embodiment, after stepping onto the patient-positioning platform, the patient would sit on the retractable seat 46 prior to proceeding with the MRI scan.

In yet another variant, the patient-positioning device 30 may remain fixed within the patient-receiving space 16, and the patient can walk into the patient-receiving space and stand on or against the patient support 38. For example, the patient may step onto the foot stand 44. Alternatively, the patient can sit on seat 46. If the equipment is to be used only in this manner, frame 32 can be fixed relative to the MRI magnet and/or integral therewith. The configuration of the magnet allows convenient walk-in patient entry.

Figure 1:
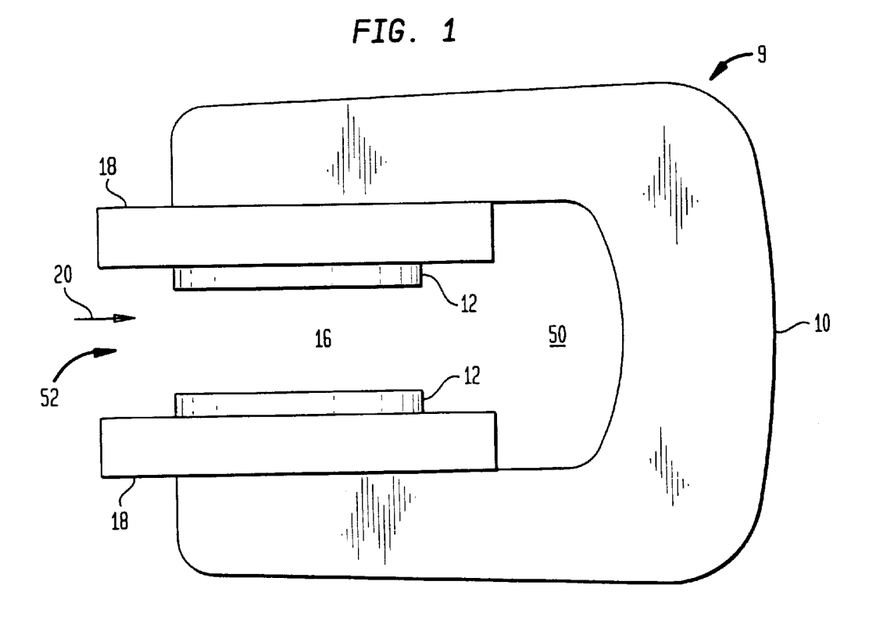
FIG. 1 is a top plan view of a magnetic resonance imaging magnet for use with the apparatus and methods in accordance with one embodiment of the invention.
Figure 2:
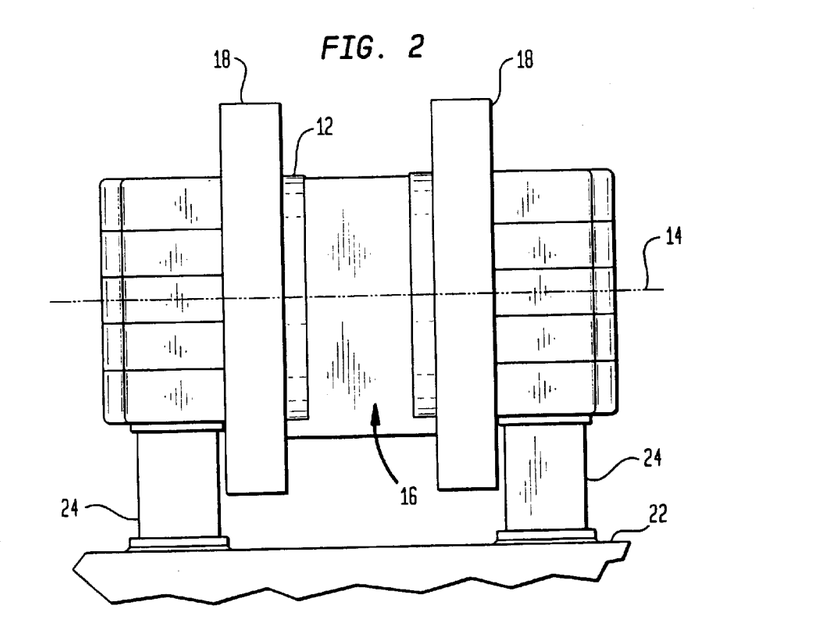
FIG. 2 is a front elevation view of the magnet of FIG. 1.
Figure 3:
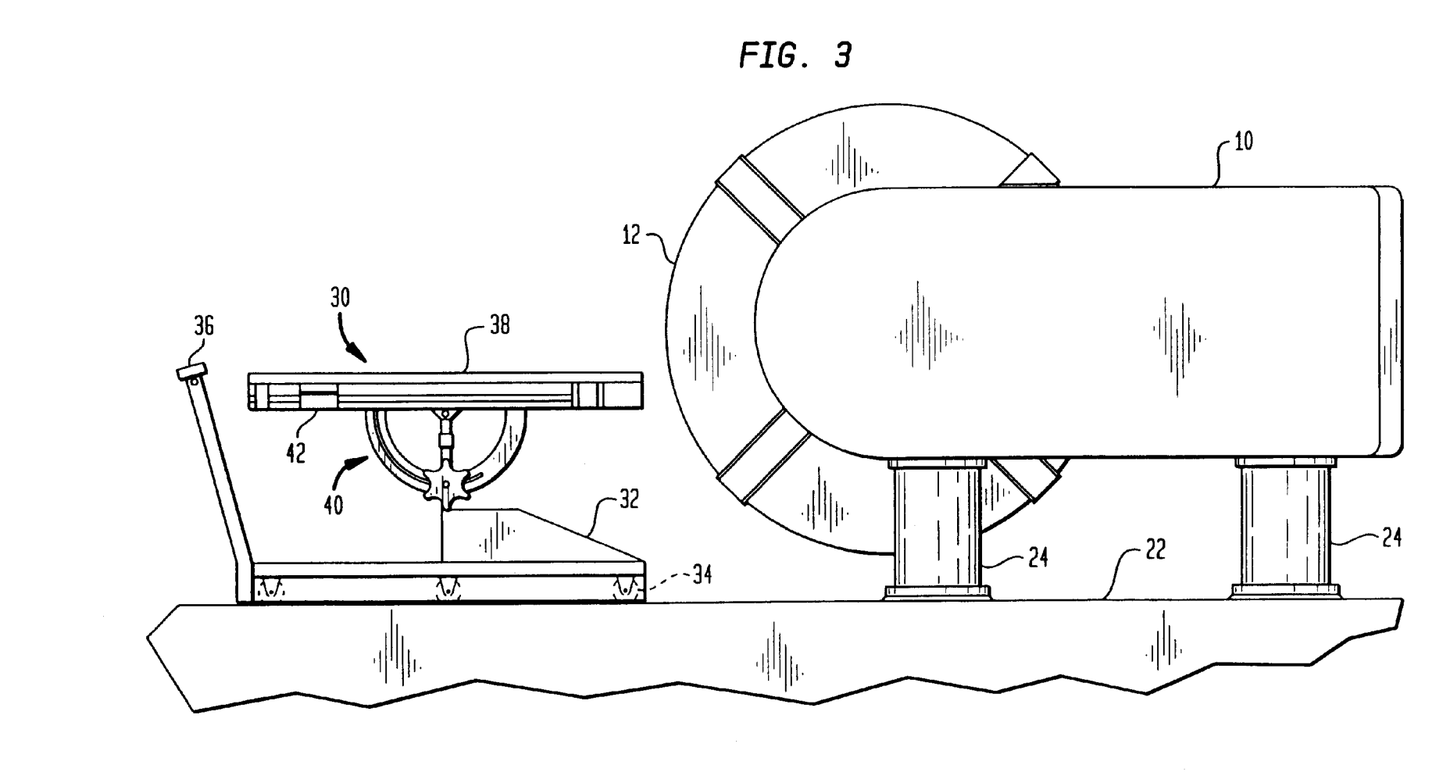
FIG. 3 is a side elevation view of the magnet and a patient-positioning device in accordance with the first embodiment of the invention.

MRI is a useful modality for monitoring the progress of surgical procedures. A further aspect of the present invention extends this utility in surgical applications, as can be seen in FIG. 1. A surgeon and associated medical personnel as necessary to perform a surgical procedure can occupy a medical personnel area 50, between the legs of the C-shaped frame and/or in the area 52 immediately outside of patient-receiving space 16. With the patient support 38 in a horizontal position, the patient is positioned in the magnet gap area, followed by the desired height adjustment as described above. The surgeon is then able to perform a surgical procedure, with the guidance of MR imaging. Such an embodiment is particularly advantageous for surgery performed on either end of the body including areas such as the head, neck or the foot ankle and knee in the case where the patient is positioned in the magnet feet-first. As an alternative embodiment, the medical personnel area may be located outside the magnet and proximate the magnet gap area, providing comparable access to the patient for surgery.

The ability to position a patient in a vertical orientation, as by positioning patient support 38 in vertical orientation with the patient either standing or sitting and perform MR imaging during a surgical procedure, enables novel surgical methods to be employed. For example, it would be advantageous to have the ability to perform intestinal or other abdominal surgery on a vertically oriented patient. Additional supports may be used to stabilize the patient when in a vertically orientated position. These supports preferably are pillows or inflatable cushions. Also, with the patient in a sitting position, a surgeon may perform knee surgery on the knee in a flexed position if desired. In these embodiments, the surgeon and associated medical personnel may operate from either medical personnel area as described above.

Figure 12:
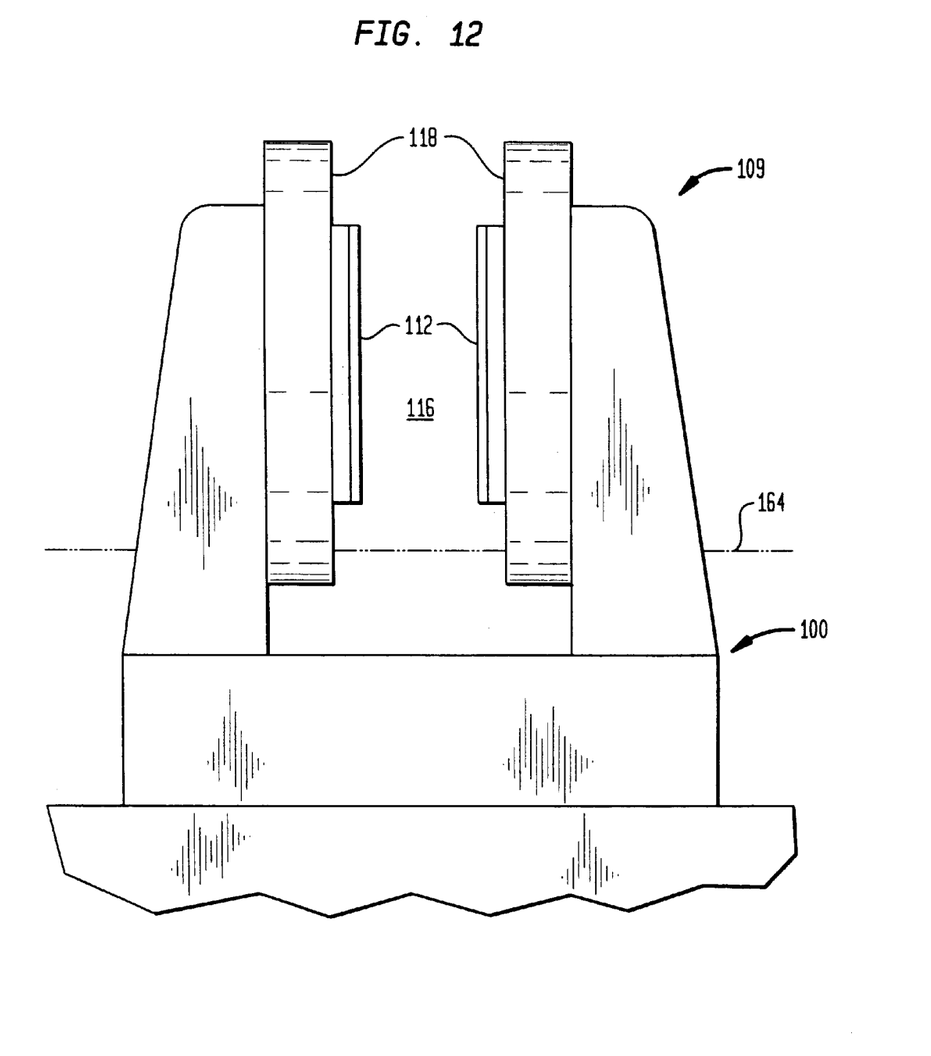
FIG. 12 is a front elevation view of the magnet of FIG. 1 in accordance with a further embodiment of the invention where the flux return frame or yoke is below a false floor.
Figure 13:
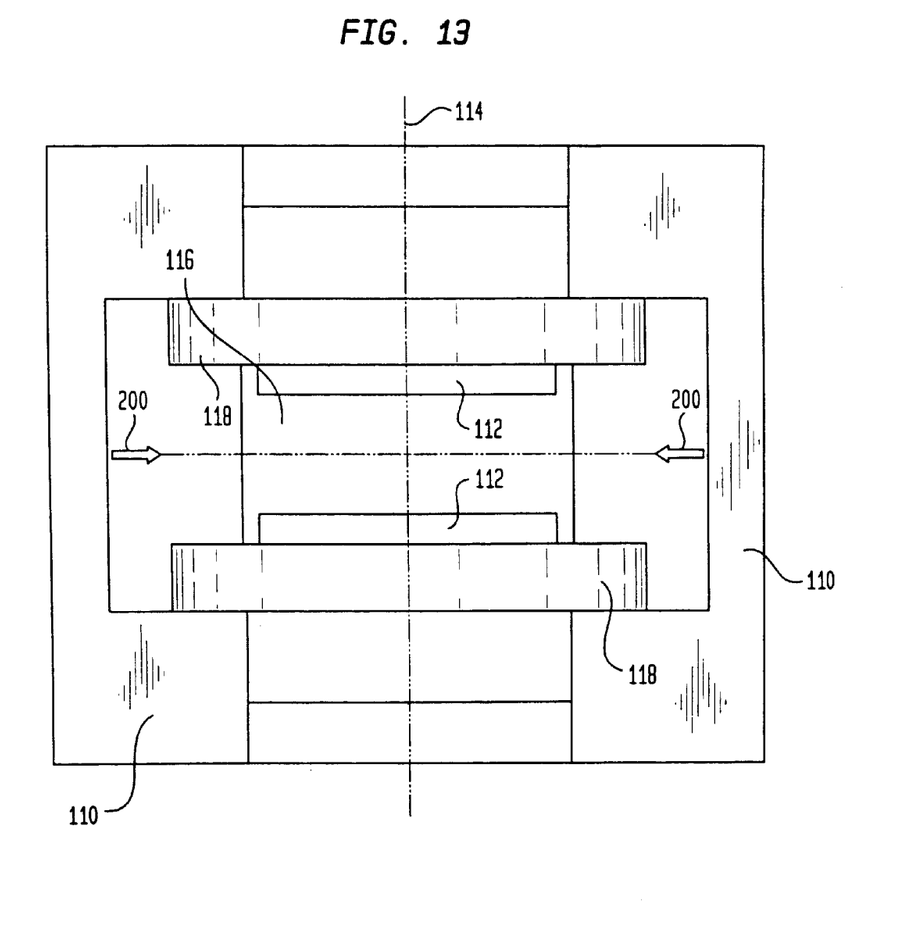
FIG. 13 is a top plan view of the magnet of FIG. 12.
Figure 14:
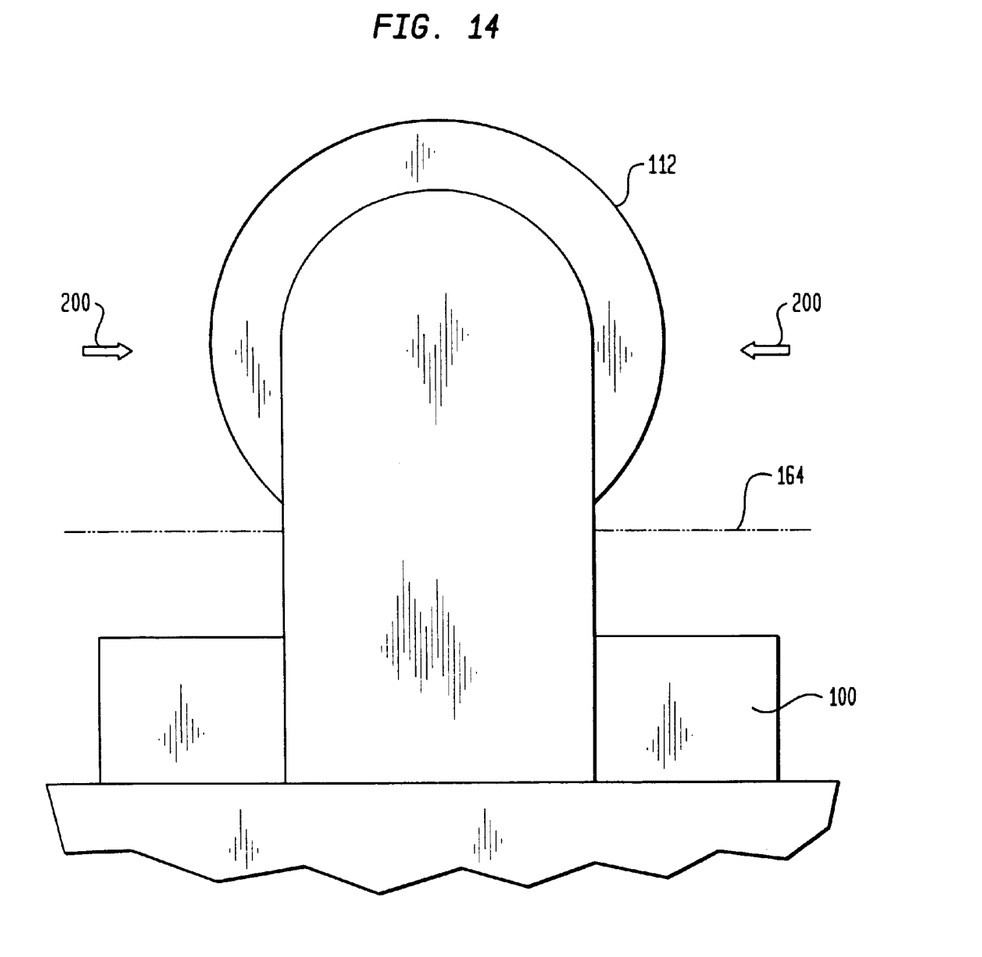
FIG. 14 is a side elevation view of the magnet of FIG. 12.

Apparatus in accordance with another embodiment of the present invention, as shown in FIGS. 12–14, includes a magnetic resonance imaging magnet 109 which may include a ferromagnetic flux return or yoke 100. In this embodiment, the yoke 100 is submerged under a false floor 164. The magnet 109 is substantially the same as the magnet 9 shown in FIGS. 1–8, wherein the yoke 100 defines a pair of opposing poles 112 projecting towards one another along a horizontally-oriented pole axis 114 (FIG. 13). A patient receiving space 116 is defined between the poles 112. Flux generating means 118 encircling portions of the frame 100 are provided.

In this particular embodiment, since the flux return yoke 100 is below the floor 164, there are two possible open directions of patient entry as indicated by arrows 200. This dual entry configuration facilitates sequential scanning of patients either in a one way direction or a two way direction. In the one way direction setup, a patient may be moved into the patient receiving space 16 while at least a second patient is prepared just outside the magnet 109 on the same side where the first patient entered the magnet. After the first patient is scanned, he or she is moved forward and out of the patient receiving space 16 to the opposite side of the magnet. Next, the second patient is moved in allowing for a continuous stream of patients with minimum downtime for the MRI scanner. In the alternative two way setup, one patient may be moved into the patient positioning space 16 from left to right, for example (FIG. 14). The second patient may be positioned outside of the magnet 109 to the right. When the first patient's scan is complete, he or she may be moved out to the left while the second patient is moved from the right to left into the patient receiving space 16. This configuration also facilitates MRI-assisted surgery and other procedures requiring medical personnel to be within the magnet's poles 120. As these and other variations and combinations of the features discussed above can be utilized, the foregoing description of the preferred embodiments should be taken by way of illustration rather than by limitation of the invention set forth in the claims.

What is claimed is:

1. A magnetic resonance imaging apparatus comprising:
   (a) a stationary magnet having a pair of elements spaced apart from one another along a horizontal axis and a patient-receiving space between said elements, said magnet being operative to direct magnetic flux between said elements through said patient-receiving space;
   (b) a patient positioning device operable to hold a patient in an upright orientation in said patient-receiving space; and
   (c) an elevator for raising or lowering the patient positioning device relative to said magnet while the patient positioning device is holding the patient in an upright orientation so as to position any part of the patient within said patient-receiving space.

2. Apparatus as claimed in claim 1 wherein said patient positioning device includes an elongated support having a long axis, said patient support being tiltable between a vertical orientation in which the long axis of the patient support extends vertically and a horizontal orientation in which the long axis of the patient support extends horizontally.

3. Apparatus as claimed in claim 2 further comprising a pivot, said patient support being tiltable about said pivot, wherein said elevator includes a linear movement device operative to move the patient support relative to said pivot so that the patient support moves vertically when the patient support is in said vertical orientation and moves horizontally when the patient support is in said horizontal orientation.

4. Apparatus as claimed in claim 3 further comprising a support frame, said pivot, said elevator and said patient positioning device being mounted to said support frame so that said patient support can be tilted relative to the support frame about said pivot and moved relative to the support frame by said linear movement device.

5. Apparatus as claimed in claim 4 wherein said support frame is movable relative to said magnet.

6. Apparatus as claimed in claim 2 wherein said patient positioning device further includes a platform projecting from said elongated support at one end thereof, whereby a patient can stand on said platform and lean against said elongated support when said support is in a substantially vertical orientation.

7. Apparatus as claimed in claim 1 wherein said patient positioning device includes a seat.

* * * * *

UNITED STATES PATENT AND TRADEMARK OFFICE
CERTIFICATE OF CORRECTION

PATENT NO.    : 6,504,371 B1                                                   Page 1 of 1
DATED         : January 7, 2003
INVENTOR(S)   : Timothy Damadian et al.

It is certified that error appears in the above-identified patent and that said Letters Patent is hereby corrected as shown below:

<u>Title page,</u>
Item [75], Inventors: "Gordon Danby" should read -- Gordon T. Danby --.

<u>Column 2,</u>
Line 44, "maintained iii the" should read -- maintained in the --.

Signed and Sealed this

Twenty-second Day of April, 2003

JAMES E. ROGAN
*Director of the United States Patent and Trademark Office*